United States Patent [19]
O'Lenick, Jr.

[11] Patent Number: 5,656,664
[45] Date of Patent: Aug. 12, 1997

[54] BRANCHED ESTERS IN SKIN CARE APPLICATIONS

[75] Inventor: Anthony J. O'Lenick, Jr., Lilburn, Ga.

[73] Assignee: Siltech Inc., Norcross, Ga.

[21] Appl. No.: 704,408

[22] Filed: Aug. 23, 1996

Related U.S. Application Data

[63] Continuation-in-part of Ser. No. 421,518, Apr. 13, 1995, Pat. No. 5,581,001.

[51] Int. Cl.$^6$ .................................................... A01N 37/02
[52] U.S. Cl. ........................... 514/552; 514/506; 514/847; 514/844; 514/873
[58] Field of Search ..................................... 514/506, 552, 514/844, 847, 873

[56] References Cited

U.S. PATENT DOCUMENTS

| | | |
|---|---|---|
| 4,425,458 | 1/1984 | Lindner ..................................... 524/314 |
| 4,868,236 | 9/1989 | O'Lenick, Jr. . |
| 5,488,121 | 1/1996 | O'Lenick, Jr. . |

Primary Examiner—Deborah D. Carr

[57] ABSTRACT

The present invention deals with the certain novel esters which are prepared by the reaction of an alpha methyl alcohol and a fatty acid. These materials are useful as conditioning agents for skin.

12 Claims, No Drawings

BRANCHED ESTERS IN SKIN CARE APPLICATIONS

RELATED APPLICATION

This application is a continuation in part of application Ser. No. 421,518 filed Apr. 13, 1995, now U.S. Pat. No. 5,581,001.

BACKGROUND OF THE INVENTION

1. Field of the Invention

The present invention deals with a process for conditioning skin which comprises contacting the skin with an effective conditioning amount of a particular group of esters made by the reaction of a high purity alpha methyl substituted alcohol and a fatty acid. These materials have outstanding liquidity, lubricating properties, resistance to oxidation, and minimal variation in viscosity as a function of temperature is required. Hair and skin are effected by environmental conditions and become dry, course and. Conditioning, as used herein, means the process by which the hair and skin are repaired from the degradation processes.

The hair and skin after a conditioning would be smoother, better hydrated, lubricated, moisturized and protected. The application of the esters of the present invention provide a thin film of an oily material to the hair and skin which allow the hair and skin to retain it's moisture, lubricate, soften and remoisturize the skin and hair.

2. Description of the Art Practices

Guerbet alcohols have been known for many years. Over the years there have been a number of derivatives patented.

U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

Fatty acid esters are a class of compounds which find applications in many diverse segments of the chemical industry. Even within an industry segment, this class of compounds are used in a wide variety of different applications. Within the personal care market segments there are several applications in which esters are useful. The first class of esters are the simple esters which function as emmolients and conditioners. These esters are generally water insoluble, and are prepared by the reaction of an alcohol and a carboxylic acid. The second class of esters are modified by the incorporation of ethylene oxide into the alcohol prior to ethoxylation. They are surface active esters that possess properties like emulsification. This article will deal only with the first type of esters, that is the simple esters.

There are numerous applications in which it is desirable to have a simple ester which is very oily, and which contributes cushion to the skin. These esters feel in many regards like mineral oil. There are likewise applications in which it is desirable for the esters to dry rapidly, giving a talc like, silky feel to the skin. It is also desirable for esters to have solvent properties to remove make up.

The specific structure of the ester determines the functional attributes of the product.

THE INVENTION

This invention relates to a process for treating the skin with an effective conditioning concentration of a particular group of esters made by the reaction of a high purity alpha methyl substituted alcohol and a fatty acid.

An additional aspect of the invention is esters made by the reaction of the high purity alpha methyl alcohol and specific guerbet acids, which are themselves highly branched. Esters so obtained not only have little variation in viscosity as a function of temperature, but are also very good moisturizing compounds when applied to the skin.

The compounds useful in the process of the present invention, are disclosed in the application from which this is a continuation in part and conform to the following structure;

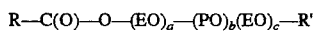

wherein;

R is selected from the group consisting of

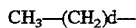

and

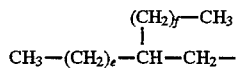

d is an integer ranging from 4 to 18;
e is an integer ranging from 1 to 16;
f is an integer ranging from 1 to 16;
EO is $(CH_2—CH_2—O)$;
PO is $(CH_2—CH(CH_3)—O—)$;
R' is

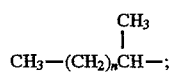

n is an integer ranging from 5 to 17;
a, b, and c are independently integers ranging from 0 to 20.

The alpha methyl alcohol is a critical ingredient for the performance of the compounds of the present invention. The availability of purified alpha methyl alcohols is a recent development. We have determined that the purity of the branched alcohol needs to be 80% by weight or greater to function in our application. If the concentration is lower, the viscosity variation as a function of temperature varies too greatly.

Alpha methyl alcohols exist as minor ingredients in oxo alcohols. These alcohols are made by the hydroformylation reaction of olefins using carbon monoxide and hydrogen according to the following reaction:

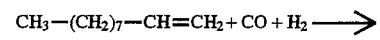

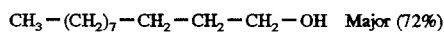

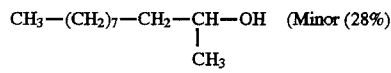

The synthesis of the compounds of the present invention using these alcohols mixed alcohols results in products which do not have the desired properties, because in part the properties of the major alcohols mask the properties of the minor alcohols. It is necessary to get the purity of the minor component up to 80% for the desired properties to appear in our application. Heretofore the purity desired was not available.

The process of the present invention is for conditioning skin and comprises contacting the skin with an effective conditioning concentration of a branched ester conforming to the following structure:

$$R-C(O)-O-(EO)_a-(PO)_b(EO)_c-R'$$

wherein;

R is selected from the group consisting of $$CH_3-(CH_2)_d-$$

and $$CH_3-(CH_2)_e-\underset{\underset{\displaystyle (CH_2)_f-CH_3}{|}}{CH}-CH_2-;$$

d is an integer ranging from 4 to 18;
e is an integer ranging from 1 to 16;
f is an integer ranging from 1 to 16;
EO is $(CH_2-CH_2-O)$;
PO is $(CH_2-CH(CH_3)-O-)$;
R' is $$CH_3-(CH_2)_n\underset{\underset{\displaystyle CH_3}{|}}{CH}-;$$

n is an integer ranging from 5 to 17;
a, b, and c are independently integers ranging from 1 to 20.

The application of the compounds of the present invention to the skin results in a moisturizing and re-fatting of the skin. This is due to the high molecular weight and low viscosity of these esters. The fact that these esters are nonirritating to the skin is another major advantage of using these compounds on the skin.

PREFERRED EMBODIMENTS

In a preferred embodiment n ranges from 9 to 15.
In a preferred embodiment d ranges from 10 to 16.
In a preferred embodiment R is $$CH_3-(CH_2)_e-\underset{\underset{\displaystyle (CH_2)_f-CH_3}{|}}{CH}-CH_2-.$$

In another preferred embodiment said branched ester conforms to the following structure:

$$R-C(O)-O-(EO)_a-(PO)_b(EO)_c-R'$$

wherein;

R is selected from the group consisting of $$CH_3-(CH_2)_d-$$

and $$CH_3-(CH_2)_e-\underset{\underset{\displaystyle (CH_2)_f-CH_3}{|}}{CH}-CH_2-;$$

d is an integer ranging from 4 to 18;
e is an integer ranging from 1 to 16;
f is an integer ranging from 1 to 16;
EO is $(CH_2-CH_2-O)$;
PO is $(CH_2-CH(CH_3)-O-)$;
R' is $$CH_3-(CH_2)_n\underset{\underset{\displaystyle CH_3}{|}}{CH}-;$$

n is an integer ranging from 9 to 17;
a, b, and c are independently integers ranging from 0 to 20.

In a preferred embodiment said effective conditioning concentration ranges from 0.1 to 100% by weight.

Raw Material Examples

Fatty Acids $$CH_3-(CH_2)_d-C(O)-OH$$

| Example | d |
|---------|----|
| A | 4 |
| B | 6 |
| C | 8 |
| D | 10 |
| E | 12 |
| F | 14 |
| G | 16 |
| H | 18 |

These materials are commercially available from a variety of sources such Henkel Corporation, Ambler Pa.

Guerbet Acids

A preferred ester is prepared using guerbet acids. Guerbet alcohols are oxidized into acids having the same regio specific beta branched properties. These properties present both in the acid and alcohol make products useful in the present invention.

$$CH_3-(CH_2)_f-\underset{\underset{\displaystyle (CH_2)_e-CH_3}{|}}{CH}-CH_2-O-H \xrightarrow{\text{oxidized}}$$
Guerbet Alcohol $$CH_3-(CH_2)_f-\underset{\underset{\displaystyle (CH_2)_e-CH_3}{|}}{CH}-C(O)-OH \quad \text{(a Guerbet acid)}$$

Vista Chemical practices the oxidation of guerbet alcohols commercially. The values of f and e were actually determined by analysis and are not dependant upon trade name for meaning.

| Example | Commercial Name | f | e |
|---------|-----------------|----|----|
| I | Isocarb 10 | 3 | 3 |
| J | Isocarb 12 | 4 | 4 |
| K | Isocarb 14 | 5 | 5 |
| L | Isocarb 16 | 6 | 6 |
| M | Isocarb 18 | 7 | 7 |
| N | Isocarb 20 | 8 | 8 |
| O | Isocarb 32 | 14 | 14 |

Isocarb is a trademark of Vista.

Branched Alcohols

This critical ingredient is available from Biosil Technologies of Englewood, N.J.. They are all over 80% purity. We have determined that the purity of 80% is critical to performance.

| | | CH₃<br>CH₃—(CH₂)ₙCH—OH | | |
|---|---|---|---|---|
| Example | a | b | c | n |
| 1 | 0 | 0 | 0 | 5 |
| 2 | 0 | 5 | 0 | 6 |
| 3 | 20 | 20 | 20 | 7 |
| 4 | 5 | 0 | 0 | 8 |
| 5 | 1 | 6 | 3 | 9 |
| 6 | 20 | 20 | 20 | 10 |
| 7 | 5 | 2 | 5 | 11 |
| 8 | 2 | 2 | 2 | 12 |
| 9 | 0 | 0 | 0 | 13 |
| 10 | 5 | 0 | 0 | 14 |
| 11 | 0 | 10 | 5 | 15 |
| 12 | 0 | 20 | 0 | 16 |
| 13 | 0 | 0 | 0 | 17 |

It will be understood that the alcohols listed above can be used as shown or combined with each other than used to synthesize the ester.

Ester Synthesis

The esterification reaction is carried out using an excess of alcohol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure

To the specified number of grams of alcohol (examples 1–13) is added the specified number of grams of the specified acid (Examples A–O). Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

| | Alcohol | | Acid | |
|---|---|---|---|---|
| Example | Example | Grams | Example | Grams |
| 14 | 1 | 130.0 | A | 116.0 |
| 15 | 2 | 439.0 | B | 144.0 |
| 16 | 3 | 2036.0 | C | 172.0 |
| 17 | 4 | 392.0 | D | 200.0 |
| 18 | 5 | 716.0 | E | 228.0 |
| 19 | 6 | 3140.0 | F | 256.0 |
| 20 | 7 | 772.0 | G | 284.0 |
| 21 | 8 | 552.0 | H | 312.0 |
| 22 | 9 | 242.0 | I | 171.0 |
| 23 | 10 | 476.0 | J | 199.0 |
| 24 | 11 | 1080.0 | K | 227.0 |
| 25 | 12 | 1464.0 | L | 255.0 |
| 26 | 13 | 298.0 | M | 283.0 |
| 27 | 1 | 130.0 | N | 311.0 |
| 28 | 2 | 439.0 | O | 479.0 |

The compounds of the invention have viscosities which vary minimally over a wide temperature range. The products made with the guerbet acid are the most preferred since they have minimal viscosity variation and are the lowest viscosity for the number of carbon atoms present.

I claim:

1. A process for conditioning skin which comprises contacting the skin with an effective conditioning concentration of a branched ester conforming to the following structure:

$$R-C(O)-O-(EO)_a-(PO)_b(EO)_c-R'$$

wherein;

R is selected from the group consisting of $$CH_3-(CH_2)_d-$$

and $$\begin{array}{c}(CH_2)_f-CH_3\\|\\CH_3-(CH_2)_e-CH-CH_2-;\end{array}$$

d is an integer ranging from 4 to 18;

e is an integer ranging from 1 to 16;

f is an integer ranging from 1 to 16;

EO is $(CH_2-CH_2-O)$;

PO is $(CH_2-CH(CH_3)-O-)$;

R' is $$\begin{array}{c}CH_3\\|\\CH_3-(CH_2)_n-CH-;\end{array}$$

n is an integer ranging from 5 to 17;

a, b, and c are independently integers ranging from 0 to 20.

2. A process of claim 1 wherein n ranges from 9 to 15.

3. A process of claim 1 wherein d ranges from 10 to 16.

4. A process of claim 1 wherein

R is $$\begin{array}{c}(CH_2)_f-CH_3\\|\\CH_3-(CH_2)_e-CH-CH_2-.\end{array}$$

5. A process of claim 1 wherein said branched ester conforms to the following structure:

$$R-C(O)-O-(EO)_a-(PO)_b(EO)_c-R'$$

wherein;

R is selected from the group consisting of $$CH_3-(CH_2)_d-$$

and $$\begin{array}{c}(CH_2)_f-CH_3\\|\\CH_3-(CH_2)_e-CH-CH_2-;\end{array}$$

d is an integer ranging from 4 to 18;

e is an integer ranging from 1 to 16;

f is an integer ranging from 1 to 16;
EO is ($CH_2-CH_2-O$);
PO is ($CH_2-CH(CH_3)-O-$);
R' is

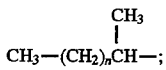

n is an integer ranging from 9 to 17;

a, b, and c are independently integers ranging from 0 to 20.

6. A process of claim 5 wherein n ranges from 9 to 15.

7. A process of claim 5 wherein d ranges from 10 to 16.

8. A process of claim 5 wherein R is

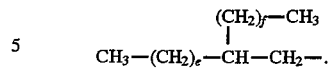

9. A process of claim 5 wherein a, b, and c are each o.

10. A process of claim 5 wherein a, b, and c are each greater than 0.

11. A process of claim 1 wherein said effective conditioning concentration ranges from 0.1 to 100% by weight.

12. A process of claim 5 wherein said effective conditioning concentration ranges from 0.1 to 100% by weight.

* * * * *